(12) United States Patent
Kasten

(10) Patent No.: US 8,935,108 B2
(45) Date of Patent: Jan. 13, 2015

(54) RHEOMETER FOR HIGH-VISCOSITY MATERIALS

(75) Inventor: Knut Kasten, Ostfildern (DE)

(73) Assignee: Putzmeister Engineering GmbH, Aichtal (DE)

( * ) Notice: Subject to any disclaimer, the term of this patent is extended or adjusted under 35 U.S.C. 154(b) by 830 days.

(21) Appl. No.: 13/118,758

(22) Filed: May 31, 2011

(65) Prior Publication Data

US 2011/0264386 A1 Oct. 27, 2011

Related U.S. Application Data

(63) Continuation of application No. PCT/EP2009/063956, filed on Oct. 23, 2009.

(30) Foreign Application Priority Data

Nov. 28, 2008 (DE) .......................... 10 2008 059 534

(51) Int. Cl.
*G01N 11/00* (2006.01)
*G01N 11/08* (2006.01)
*G01N 11/12* (2006.01)

(52) U.S. Cl.
CPC ................ *G01N 11/08* (2013.01); *G01N 11/12* (2013.01)
USPC .......................... 702/50; 73/54.01; 73/54.09

(58) Field of Classification Search
USPC ............ 702/50, 100; 73/54.01, 54.07, 54.09, 73/521
See application file for complete search history.

(56) References Cited

U.S. PATENT DOCUMENTS 3,839,901 A * 10/1974 Finkle et al. ................. 73/54.01
3,911,728 A * 10/1975 Fixot ............................. 73/54.04

(Continued)

FOREIGN PATENT DOCUMENTS

DE 3933973 A1 4/1991
GB 2 347 749 A 9/2000

OTHER PUBLICATIONS

International Search Report dated Aug. 31, 2010 of international application PCT/EP 2009/063956 on which this application is based.

(Continued)

*Primary Examiner* — Manuel L Barbee
(74) *Attorney, Agent, or Firm* — Walter Ottesen P.A.

(57) ABSTRACT

The invention relates to a rheometer (100) for high-viscosity materials and to a device and a method for estimating, by means of such a rheometer (100), the feeding pressure to be applied in order to overcome the feeding resistance of high-viscosity material in a pipe. The rheometer (100) has a receptacle for holding high-viscosity material in the receptacle. The receptacle is designed as a standard pipe section (102) that can be filled with high-viscosity material (300). In the rheometer (100), the standard pipe section (102) and high-viscosity material (300) filled into the standard pipe section (102) can be made to linearly move relative to each other at a first rate and at another rate differing from the first rate. A unit (146, 147, 148) for determining a rate of the relative movement of the high-viscosity material (300) and the standard pipe section (102) as well as a unit (160) for determining a pressure applied to the high-viscosity material (300) as a result of the relative movement of the high-viscosity material (300) and the standard pipe section (102) are provided as a measuring instrument.

24 Claims, 10 Drawing Sheets

(56) References Cited

U.S. PATENT DOCUMENTS

| | | | |
|---|---|---|---|
| 4,241,602 A | | 12/1980 | Han et al. |
| 4,313,339 A | * | 2/1982 | Nichols et al. ............... 73/54.14 |
| 4,539,837 A | * | 9/1985 | Barnaby ...................... 73/54.06 |
| 5,209,108 A | * | 5/1993 | Shackelford ................ 73/54.28 |
| 5,900,539 A | | 5/1999 | Tremblay et al. |
| 6,581,440 B1 | | 6/2003 | Rupieper et al. |
| 7,681,437 B2 | | 3/2010 | Brinz et al. |

OTHER PUBLICATIONS

International Preliminary Report on Patentability of the International Searching Authority (Form PCT/IPEA/409) Jan. 14, 2011 (translation into English).

* cited by examiner

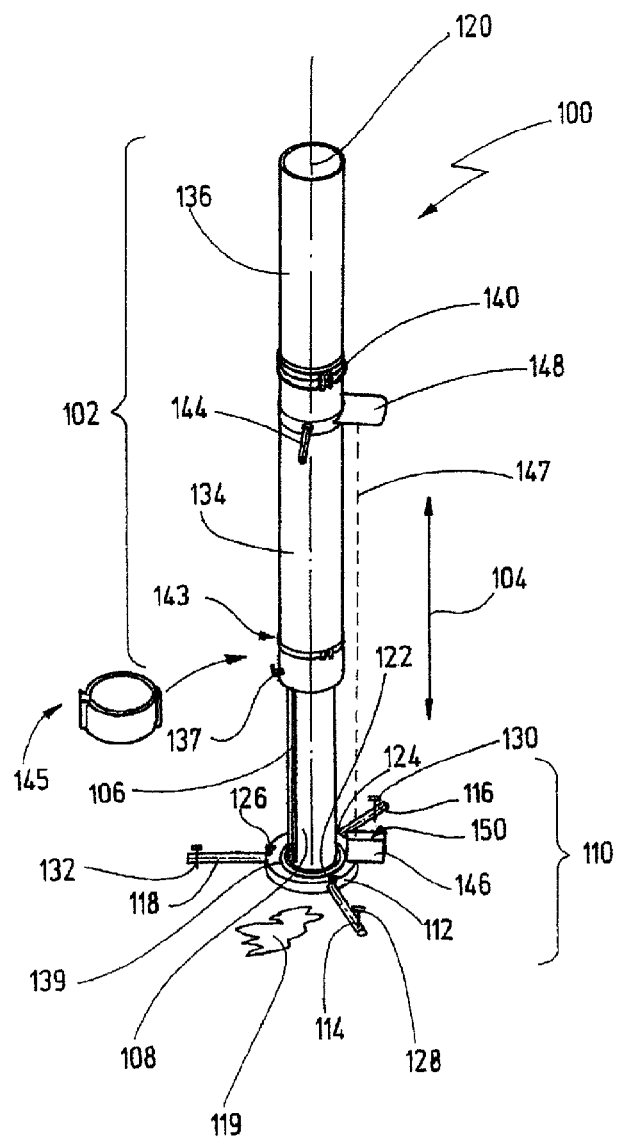
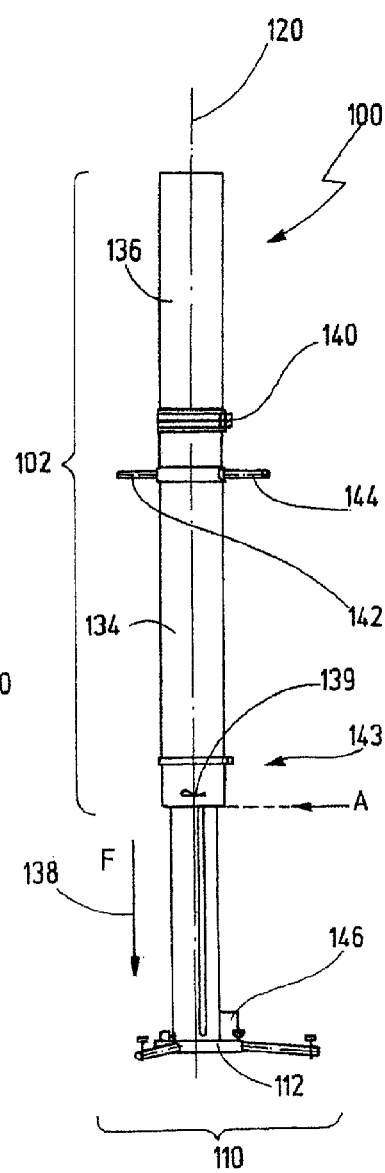
Fig.1a
Fig.1b

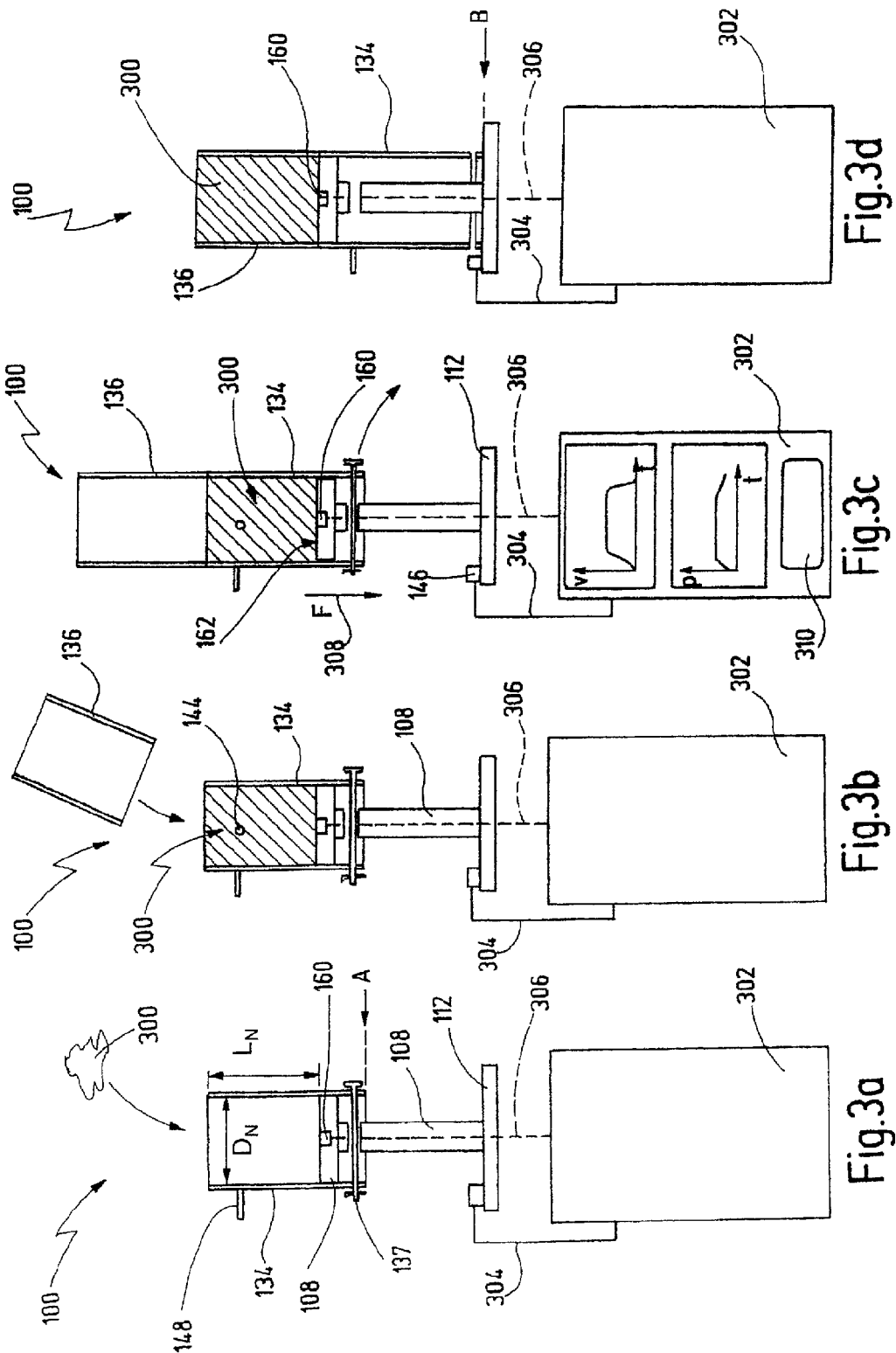

RHEOMETER FOR HIGH-VISCOSITY MATERIALS

CROSS REFERENCE TO RELATED APPLICATIONS

This application is a continuation application of international patent application PCT/EP 2009/063956, filed Oct. 23, 2009, designating the United States and claiming priority from German application 10 2008 059 534.9, filed Nov. 28, 2008, and the entire content of both applications is incorporated herein by reference.

FIELD OF THE INVENTION

The invention relates to a rheometer for high-viscosity materials having a vessel for accommodating high-viscosity material and having a measuring device for the flow behavior of high-viscosity material in the vessel. The invention further relates to an arrangement for determining the feeding resistance of high-viscosity material in a pipeline system as well as a method of the feeding pressure to be developed for overcoming the feeding resistance of high-viscosity materials in a pipeline system.

BACKGROUND OF THE INVENTION

A rheometer is a measuring apparatus for determining the flow behavior of materials. Rheometers of the above-mentioned type are known in the configuration of the rotation rheometer and, for example, are described in "Comparison of concrete rheometers: International tests at LCPC (Nantes, France) in October, 2000, NISTIR 6819". These rheometers have a vessel fillable with high-viscosity material and a measuring device having a rotationally movable measuring geometry for measuring torque. With a rotational movement of the measuring geometry, a torque develops because of the high-viscosity material filled in the vessel, which torque is measured. From this, the flow behavior of the high viscosity material can be determined.

The flow behavior of high-viscosity materials determines their processability, compressibility, and feedability.

In pipelines, for feeding high-viscosity materials such as concrete or sludge, coal slurry, or biological waste, a feeding resistance develops which is dependent upon the flow behavior of the high-viscosity material. A reason for the feed resistance is the friction of the high-viscosity material with the pipeline wall and the deforming work which occurs on the high-viscosity material during transport through a pipeline. The deforming work is caused by the inner deforming resistance of the high-viscosity material.

Due to the feeding resistance, a high-viscosity material pump for feeding the high-viscosity materials over an elevation difference Δh through a pipeline system must generate not only a pressure $P_{\Delta h}$ which corresponds to the pressure which a high-viscosity material column causes over an elevation difference Δh at the output of the high-viscosity material pump in the connecting region of the pipeline system, but also an additional pressure $P_{FW}$.

For the pressure $P_{\Delta h}$, the following applies as a rule:

$$P_{\Delta h} = g \rho \Delta h, \quad (1)$$

wherein g is the gravitational acceleration and ρ is the density of the high-viscosity material. The additional pressure $P_{FW}$ must be developed in order to overcome the above-mentioned feeding resistance in the pipeline system.

The consequence is that a high-viscosity material pump must make available at least the feeding pressure $$P_F = P_{FW} + P_{\Delta h} \quad (2)$$

in order to feed the high-viscosity material over the elevation difference Δh through the pipeline system.

It is known, for the feeding of pumped concrete through a pipeline system having a given pipeline diameter D and a given pipeline length L, at a desired delivery volume and a specific pumped concrete consistency classified by the slump according to DIN EN 12350-5, to estimate the necessary pressure $P_{FW}$ for overcoming the feeding resistance by means of a nomogram. The slump according to DIN EN 12350-5 is applied as a measure for the flow behavior of concrete. This method of estimating $P_{FW}$ is based on experience values or on a set of measuring data which was recorded for numerous types of pumped concrete of different pipeline systems. One such nomogram is illustrated and shown e.g. on page 53 of the Putzmeister corporate brochure "Betontechnologie für Betonpumpe".

With a known density $p_{PB}$ of the pumped concrete and a given delivery head Δh of a pipeline system with pipeline length L a conclusion can be drawn as to the feeding pressure $P_F$ with this nomogram for a desired delivery volume Q of pumped concrete per time unit.

It is shown, however, that this approach is suitable only for estimating $P_{FW}$ for so-called simple pumped concrete, that is, when the pumped concrete is a ternary mixture comprising admixtures, water and cement as main components. If, for example, simple pumped concrete is mixed with additional substances or admixtures such as plasticizers for specific applications, the flow behavior of concrete is no longer appropriately characterized by the slump according to DIN EN 12350-5. Therefore, for pumped concrete having admixtures, the required feed pressure $P_F$ for a pipeline system can no longer be estimated well with the above nomogram.

The known rotation rheometers for high-viscosity materials are not suited either to determine the flow behavior of concrete in such a manner that required feed pressure $P_F$ can be ascertained in a reliable manner therefrom.

To determine the feeding pressure $P_F$ required in a pipeline system for pumped concrete, to which admixtures are added, or to ascertain a feeding pressure $P_F$ for other high-viscosity materials, such as sludge, coal slurry or biological waste, so far difficult pumping attempts have been carried out: The corresponding high-viscosity material is pumped through a test construction having the pipeline system provided for the specific application. On the test construction, the pressure conditions in the pipeline system are then detected for different feeding velocities of the high-viscosity material. In particular in the region connecting the high-viscosity material pump and the pipeline system the pressure occurring is measured. This measured pressure then corresponds to the feeding pressure $P_F$.

SUMMARY OF THE INVENTION

Starting from the above, it is an object of the invention to provide a rheometer with which the flow behavior of high-viscosity material, in particular, of concrete can be determined in such a manner that the required feeding pressure in a pipeline system can be estimated in a reliable manner.

Furthermore, it is another object of the invention to provide an apparatus of a simple design and suitable for mobile employment; by means of which for a given pipeline system, for a specific high-viscosity material to be fed, and for a desired delivery volume Q of high-viscosity material per time unit, the pressure $P_{FW}$ can be estimated, which must be produced by a high-viscosity material pump in order to overcome the feeding resistance occurring in the pipeline system. Moreover, it is still another object of the invention to provide a method by means of which the corresponding pressure $P_{FW}$ can be ascertained in a fast, simple manner and at a low expense at the specific place of use of a thick-viscosity material pump.

The rheometer of the invention is for high-viscosity materials. The rheometer includes: a vessel assembly including a pipe section fillable with the high-viscosity material and a piston movable at a velocity (v) relative to the pipe section; the piston being arranged in the pipe section so as to cause the high-viscosity material to act on the piston with a pressure (P); a measuring arrangement including a first unit for measuring the velocity (v) and a second unit for measuring the pressure (P); and, a computer unit for carrying out a computation of the flow behavior of the high-viscosity material in the vessel assembly based on the velocity (v) and the pressure (P).

One finding of the invention is that thus the flow behavior of high-viscosity materials in a pipeline system can be measured, for which there does not exist a linear relationship between the pressure $P_{FW}$ for overcoming the feeding resistance and the delivery volume Q.

With respect to some non-thixotropic high-viscosity materials such as e.g. concrete, one finding of the invention relates to the fact that in the case of laminar flow in a straight pipeline section i having the length $L_i$ and the diameter D there exists the below relationship between the pressure drop $P_i$, which is caused by the feeding resistance of the high-viscosity material in the pipeline section i and the delivery volume Q of high-viscosity material per time unit through the pipeline section i:

$$P_i = \tau_{DS} \frac{L_i}{D_i} + b_{DS} \frac{L_i}{D_i^{\alpha_{DS}}} Q, \quad (3)$$

whereby, as a matter of fact, the equation parameters $\tau_{DS}$ and $b_{DS}$ and the power $\alpha_{DS}$ depend on the type of high-viscosity material but have an invariance as compared to common pipe wall qualities and in particular are independent of the magnitude of the delivery volume Q.

Another finding consists in that when feeding non-thixotropic high-materials through a straight pipeline section or through a pipeline section j, which comprises a reduction portion for narrowing the effective diameter of the pipeline, or through a pipeline section in which a curved piece is provided, e.g. a 90° curve or a 180° curve, the following relationship exists between the pressure for overcoming the feeding resistance $P_j$ in the pipeline section j and the delivery volume Q independent of the composition of the high-viscosity material in certain non-thixotropic high-viscosity materials, such as e.g. concrete:

$$P_j = A_j + B_j Q, \quad (4)$$

wherein, as a matter of fact, the parameters $A_j$ and $B_j$ depend on the type of high-viscosity material fed and on the geometry of the respective pipeline section j but are approximately independent of the delivery volume Q fed through the pipeline section.

Furthermore, the solution according to the invention is based on the finding that for feeding high-viscosity material through a pipeline system which consists of pipeline sections i of length $L_i$ and diameter $D_i$ as well as pipeline sections j, in which narrowed portions and curved pieces are designed, for the purpose of overcoming the feeding resistance the pressure $$P_{FW} = \sum_i P_i + \sum_j P_j \quad (5)$$

must be generated, whereby the equations (3) and (4) apply for $P_i$ and $P_j$.

In particular, the solution of the invention is based on the finding that by adjusting a movement of a high-viscosity material column, which is accommodated in a standard pipeline section, relative to the standard pipeline section by moving the standard pipeline section relative to the high-viscosity material column and thereby the high-viscosity material column remains stationary, the flow behavior of the high-viscosity material in a pipeline system can be simulated appropriately: By means of a simple pressure measurement, at different relative velocity courses a correct conclusion can be made as to the flow behavior of the high-viscosity material in the pipeline system. One finding of the invention also lies in the fact that the standard pipeline section can be comparatively short: A standard pipeline section of e.g. 1 m in length, which is suited for accommodating a 50 cm high high-velocity material column, is sufficient to correctly estimate the flow behavior of the high-viscosity material in a pipeline system that may be several hundred meters long.

Accordingly, the invention proposes, for one thing, a rheometer which is particularly suited for the use in laboratories and on construction sites, with which for a given high-viscosity material the feeding pressure $P_{FW}$ for a given delivery volume Q, which pressure is necessary to overcome the feeding resistance in a standard pipeline section can be directly measured, and the invention specifies an easy-to-use apparatus and an easy-to-use method by means of which the feeding pressure $P_{FW}$ to be applied can be reliably estimated in order to feed a certain high-viscosity material with the feeding quantity Q through a pipeline system.

A peculiarity of the invention consists in that as a means for generating a relative movement of standard pipeline section and high-viscosity material there is provided a piston acting upon the high-viscosity material in the standard pipeline section, whereby the standard pipeline section is movably arranged relative to the piston. This makes possible a simple and sturdy construction of the rheometer.

A preferred embodiment of the invention provides that the standard pipeline section is forcibly guided for a straight-linear movement from a first to at least another position. Advantageously, the rheometer has a latching mechanism in order to fix the standard pipeline section in a first and/or second position. Advantageously, a carrier unit is provided for accommodating the standard pipeline section and the piston. It is advantageous to arrange the piston of the apparatus on the carrier unit in an unmovable, that is stationary manner.

A preferred embodiment of the invention consists in that for the determination of the pressure acting on the high-viscosity material due to the relative movement of the high-viscosity material and the standard pipeline section a pressure sensor attached on the piston or a force sensor integrated in the piston is provided.

By providing a means for generating a drive force for causing a relative movement of standard pipeline section and piston, also high-viscosity materials having a large inner deforming resistance can be examined. Here, it is advantageous to adapt the means for generating a drive force for the generation of drive forces of different quantity. In particular, the means can also comprise a drive cylinder, for instance, a hydraulically actuated drive cylinder. A particularly simple means for generating a corresponding drive force consists in a load weight. When the load weight is designed in a variable manner, different relative movement courses of standard pipeline section and high-viscosity material can be adjusted by means of varying the load weight.

A special embodiment of the invention provides to adapt a reduction of the inner diameter on the standard pipeline section or to provide a curved piece. Thus, for a certain high-viscosity material the feeding resistance of reducing portions and curved pieces in a standard pipeline section can be ascertained.

For an operator to be able to control the flow behavior of the high-viscosity material in the measuring device it is advantageous to design the standard pipeline section at least partially of transparent plastic.

It is advantageous to provide for the standard pipeline section a first and a second standard pipeline section as well as possibly any other standard pipeline sections which can be connected to or separated from one another. This allows simple filling and emptying of the rheometer.

Attaching at least one handle to the standard pipeline section guarantees a comfortable manual operability of the rheometer. In particular, the manual generation of a drive force is made possible in order to move the standard pipeline section relative to the piston.

By providing a means for charging high-viscosity material accommodated in the standard pipeline section with a static pressure, the flow behavior of the high-viscosity material under pressure load can be determined.

BRIEF DESCRIPTION OF THE DRAWINGS

The invention will now be described with reference to the drawings wherein:

FIGS. 1a and 1b are a first and second perspective view of a first rheometer shown in a first set position;

FIGS. 3a to 3f are schematic views of the first rheometer for illustrating a measuring operation;

DESCRIPTION OF THE PREFERRED EMBODIMENTS OF THE INVENTION

Figure 2:
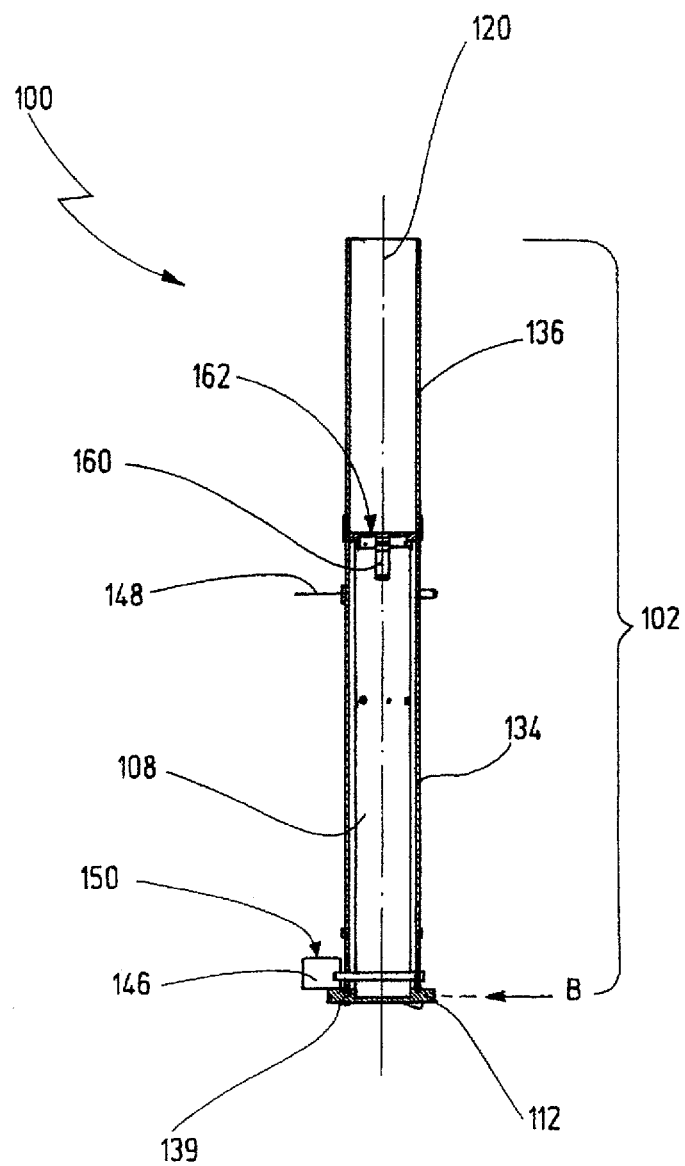
FIG. 2 is a section view of the first rheometer in a second set position.

The rheometer 100 shown in FIGS. 1a and b includes, as a vessel for high-viscosity material, a standard pipe section 102 fillable with the high-viscosity material. A piston 108 is assigned to the standard pipe section 102 which projects into the standard pipe section 102. The standard pipe section 102 is open at one end at the end lying opposite to the piston 108. The standard pipe section 102 can be moved along a straight line in correspondence to the double arrow 104 relative to the piston 108. For this purpose, the standard pipe section 102 is guided parallely in a constraining guide 106 on the piston 108 projecting into the standard pipe section 102. In order to be able to observe the piston 108 and a high-viscosity material, which is filled into the standard pipe section 102, the standard pipe section 102 is preferably made of a transparent material, for example, a transparent plastic.

The piston 108 is fixed to be stationary on an adjustable carrier unit 110. The carrier unit 110 includes a carrier plate 112 on which three support feet (114, 116, 118) are formed which function to support the apparatus on the base 119, if needed, also in the earth region at a building site.

The carrier unit 110 facilitates a vertical, that is a perpendicular alignment of the axis 120 of the standard pipe section 102 and piston 108. For this purpose, the three support feet (114, 116, 118) are held by means of wing screws (122, 124, 126) in bores on the carrier plate 112, which screws are inclined at an angle toward the base 119 with reference to the axis 120 of the standard pipe section 102 and piston 108. Adjustable wing screws (128, 130, 132) are provided at the ends of the support feet. The axis 120 of the standard pipe section 102 and the piston 108 can be vertically aligned by means of the wing screws (128, 130, 132).

The standard pipe section 102 is configured as two parts. It includes a unit 134 and a pipe segment unit 136. The pipe segment unit 136 and the unit 134 are connected by means of a connecting mechanism 140. The connecting mechanism 140 permits a rapid opening and closing. This makes it possible to remove the pipe segment unit 136 from the unit 134 of the standard pipe section 102 or to attach it to the unit 134. With the pipe segment unit 136 removed, the standard pipe section 102 can be easily and comfortably filled with high-viscosity material by a service person.

A releasable latching mechanism 137 is formed on the unit 134 of the standard pipe section 102. The latching mechanism 137 serves to secure the standard pipe section 102 on the piston 108 in the position A shown in FIGS. 1a and 1b.

In order to make a good estimate of the feeding pressure for a pipeline system, the pipe segment unit 136 and the unit 134 preferably have a pipe diameter corresponding to the pipe diameter of the pipeline system for which the estimate of the feeding pressure is of interest.

Here, the pipe segment unit 136 and the unit 134 have a pipe diameter of 12.5 cm. The length of the unit 134 is designed such that a 50 cm high column of high-viscosity material is disposed above the piston 108 when the unit 134 is completely filled with high-viscosity material. The dead weight of the standard pipe section is approximately 2.5 kg.

When the latching mechanism 137 is released, the weight force acting on the standard pipe section 102 acts as a drive force and moves the standard pipe section downwardly in the direction of the carrier plate 112 of the carrier unit 110 in accordance with the arrow 138. A slot 139 is formed in the carrier plate 112 as an end stop for the standard pipe section 102, which slot 139 is designed with an element for damping an impact of the standard pipe section 102.

A first handle 142 and a second handle 144 are provided on the unit 134. The standard pipe section 102 can be moved by muscle power by means of handles (142, 144) on the piston 108 by a service person when the latching mechanism 137 is open.

The standard pipe section 102 has a receiving section 143 for an ancillary weight 145 configured as a pipe clamp. The weight force F, which acts on the standard pipe section 102, is increased in correspondence to the dead weight of the pipe clamp in that the pipe clamp 145 is attached to the standard pipe section 102.

The rheometer 100 has a measuring device having a unit for the determination of the relative movement of the high-viscosity material and the standard pipe section 102 in the form of a laser displacement transducer 146. Allocated to the laser displacement transducer 146 is a plate 148 at least partially reflecting a laser beam 147, which plate 148 is attached to the standard pipe section 102. By means of the laser displacement transducer 146, it is possible to measure the distance of the plate 148 from the front face 150 of the laser displacement transducer 146 as a function of time. In this way, the laser displacement transducer can detect an instantaneous movement velocity of the standard pipe section 102 at the piston 108. The laser displacement transducer 146 is connected to a computer unit (not shown in FIGS. 1a and b) for controlling the signal evaluation.

It is noted that also a displacement transducer of another configuration or even a velocity or acceleration measuring device can be used in lieu of the laser displacement transducer for the determination of a relative movement of the high-viscosity material and the standard pipe section.

FIG. 2 shows a section of the rheometer 100 of FIGS. 1a and b, whereby the standard pipe section is moved into a position B on the damping element in the slot 139 of the carrier plate 112. The same reference numerals are used in FIG. 2 as are used in FIGS. 1a and 1b for identifying the same components.

A pressure sensor 160 configured as a concrete pressure sensor is provided in the rheometer 100 as a measuring device, by means of which a pressure acting on the high-viscosity material due to the relative movement of high-viscosity material and standard pipe section 102, by means of detecting a pressure force can be determined. The pressure sensor 160 is accommodated centrally on the front face 162 of the piston 108. It is likewise connected to the above-mentioned computer unit for the purpose of control and signal evaluation.

The operation of the rheometer 100 described with respect to FIGS. 1a and 1b as well as FIG. 2 is shown in more detail in FIGS. 3a to 3f. The components of the rheometer in FIGS. 3a to 3f are only shown schematically. The reference numerals of FIGS. 1a and 1b as well as FIG. 2 are used for explanation insofar as they refer to identical components.

FIG. 3a shows the computer unit 302 for the control and signal evaluation, to which the laser displacement transducer 146 and the pressure sensor 160 are connected via data transmission elements (304, 306). To prepare the rheometer 100 for a measuring operation, first, unit 134 of the standard pipe section 102 is latched in the position A shown in FIG. 3a to the piston 108 by means of the latching mechanism 137.

Thereafter, and as shown in FIG. 3b, the unit 134 of the standard pipe section having a pipe diameter $D_N$ is filled to the top edge over a length $L_N$ with a high-viscosity material 300 whose feeding resistance is to be determined.

In a next step according to FIG. 3c, the pipe segment unit 136 is seated on the unit 134 of the standard pipe section 102 and is latched therewith.

First, for a latched rheometer, the pressure $P_M$ loading the piston due to the high-viscosity material 300 is first determined by means of the pressure sensor 160 mounted on the piston 108.

Neglecting the friction of the high-viscosity material on the inner wall of the standard pipe section 102, the mass M of the high-viscosity material accommodated in the standard pipe section 102 results as follows:

$$M = \frac{D^2}{4g}\pi P_M, \tag{7}$$

wherein g is the gravitational acceleration and D is the inner diameter of the standard pipe section 102. In this way, a determination of the density $\rho_B$ of the high-viscosity material, which is filled in the standard pipe section 102, is possible with the rheometer 100. Accordingly, the following applies:

$$\rho_B = \frac{M}{V}, \tag{8}$$

wherein V is the volume of the high-viscosity material filled in the standard pipe section 102.

Thereafter, the latching mechanism 137 is released. The consequence is that the standard pipe section 102 is moved toward the carrier plate 112 due to the gravitational force F which acts in the direction of the arrow 308. The standard pipe section 102 is accelerated by the gravitational force F to a friction-condition limit velocity $v_{G1}$. It then sinks at the velocity $v_{G1}$ toward the carrier plate 112. Then, by means of the pressure sensor 160, the pressure P(t) caused by the high-viscosity material 300 on the front face 162 of the piston 108, and the movement velocity v(t) of the standard pipe section 102 via the laser displacement transducer 146 on the piston 108 as a function of time t are measured.

FIG. 3d shows the standard pipe section which is filled with high-viscosity material 300 at the position B on the carrier plate 112.

Figure 3F:
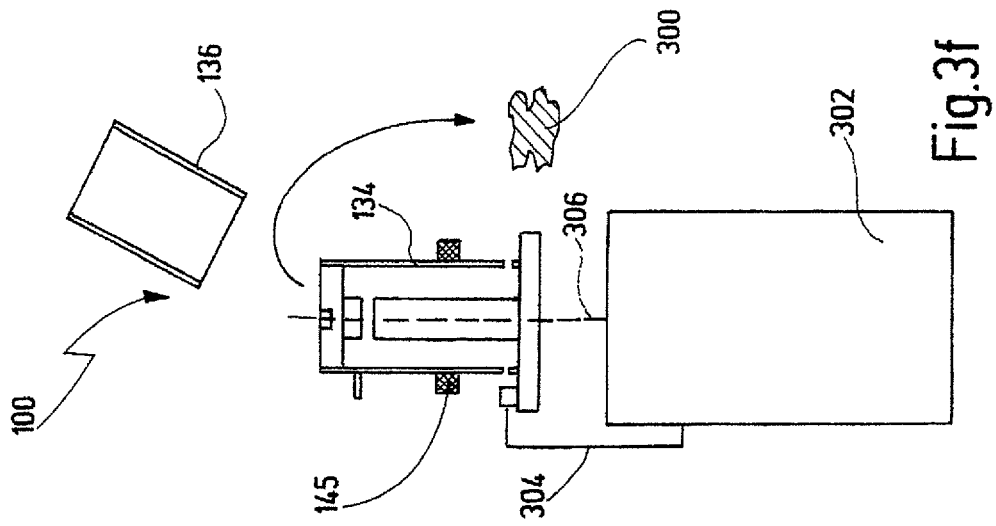
Figure 3E:
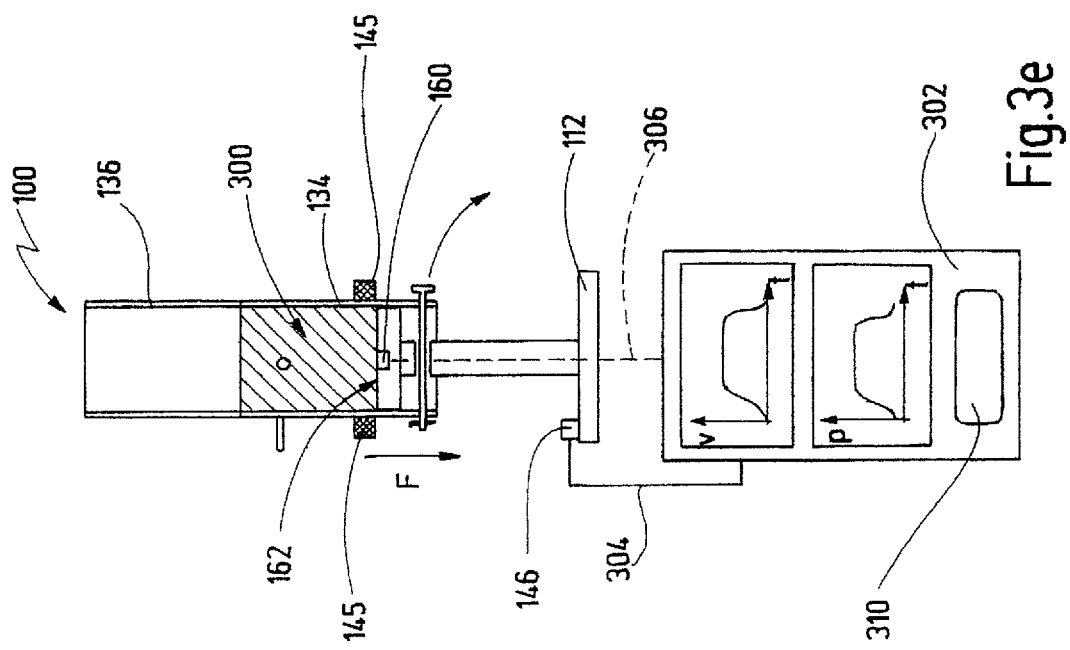

This measurement of pressure P(t) and the movement velocity v(t) is, as shown in FIG. 3e, repeated with the ancillary weight 145, which is provided for the standard pipe section 102: Due to the now greater gravitational force the standard pipe section 102 is accelerated to the limit velocity $v_{G2}$ descending on the piston 108.

If required, the ancillary weight 145 is changed once again in order to then record corresponding pressure and velocity courses ($P_n$, $v_{Gn}$).

Thereafter, the computer unit 302 ascertains, from the detected time courses for pressure P(t) and the velocity v(t), the pressure $P_1$ to $P_n$ resulting at the limit velocity $v_{G1}$ to $v_{Gn}$ and/or the delivery volumes $Q_1$ to $Q_n$ in order to display with the aid of the values a diagram of the dependence of P and Q on the display 310.

For this purpose, in the computer unit 302, for the equation system $$P_1 = \tau_{DS}\frac{L_N}{D_N} + b_{DS}\frac{L_N}{D_N^{a_{DS}-2}}\frac{\pi}{4}v_{G1} \tag{6}$$

$$P_n = \tau_{DS}\frac{L_N}{D_N} + b_{DS}\frac{L_N}{D_N^{a_{DS}-2}}\frac{\pi}{4}v_{Gn}$$

the parameters $\tau_{DS}$ and $b_{DS}$ are determined and displayed on the display unit 310 of the computer unit 302.

To remove the high-viscosity material 300 from the standard pipe section, as shown in FIG. 3f, the pipe segment unit 136 is separated from the unit 134 by loosening the provided latching mechanism in order to release the accommodated high-viscosity material 300.

Figure 4:
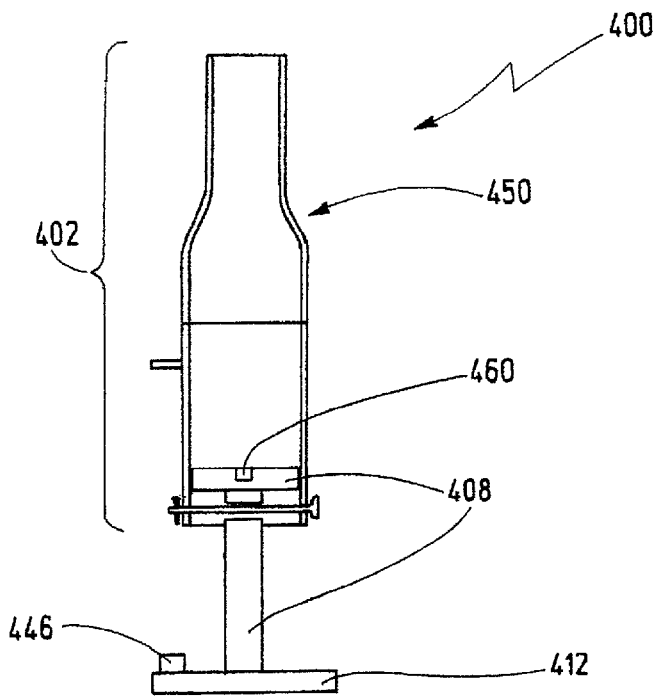
FIG. 4 is a schematic view of a second, modified rheometer.

FIG. 4 shows a rheometer 400 having a standard pipe section 402 wherein a diameter reduction 450 is formed in order to make possible an estimate of the feeding resistance caused by a reducer in the pipeline system. Incidentally, the function of the rheometer 400 corresponds to that of the rheometer 100 which is explained with reference to FIGS. 1, 2 as well as FIGS. 3a-f. Components of the rheometer 400, which are also present in the rheometer 100, have reference numerals increased by 300 with respect to FIGS. 1 and 2.

Figure 5:
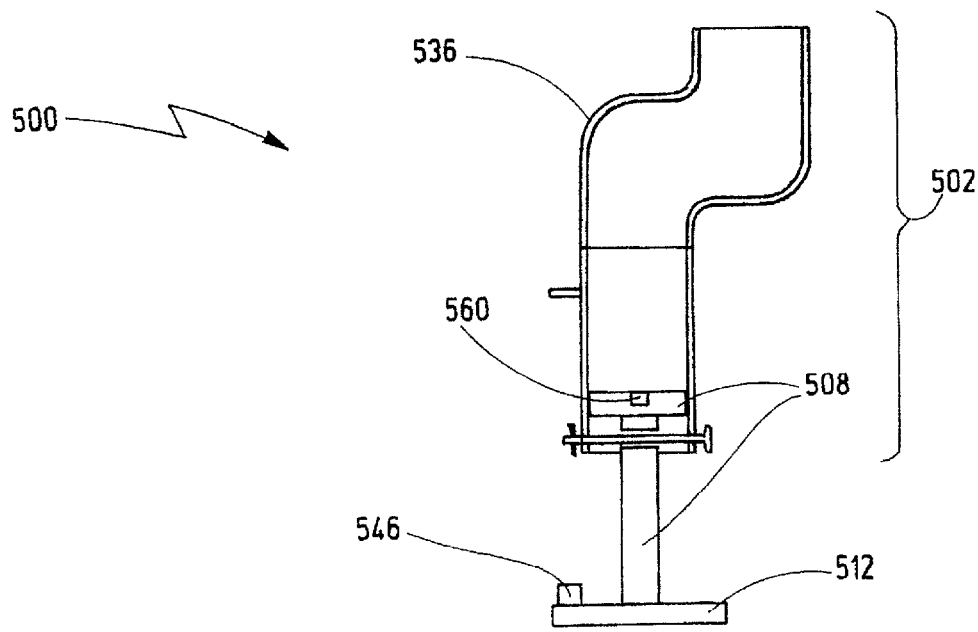
FIG. 5 is a schematic view of a third, modified rheometer.

FIG. 5 shows a rheometer 500 having a standard pipe section 502 wherein a curved piece 536 is present. The rheometer 500 makes possible an estimation of the feeding resistance which is caused by a corresponding curved piece in a pipeline system for high-viscosity materials. Incidentally, the mode of operation of the rheometer 500 corresponds to that of the rheometer of FIG. 4, and correspondingly identical components are identified in FIG. 5 by reference numerals increased by 100.

Figure 6:
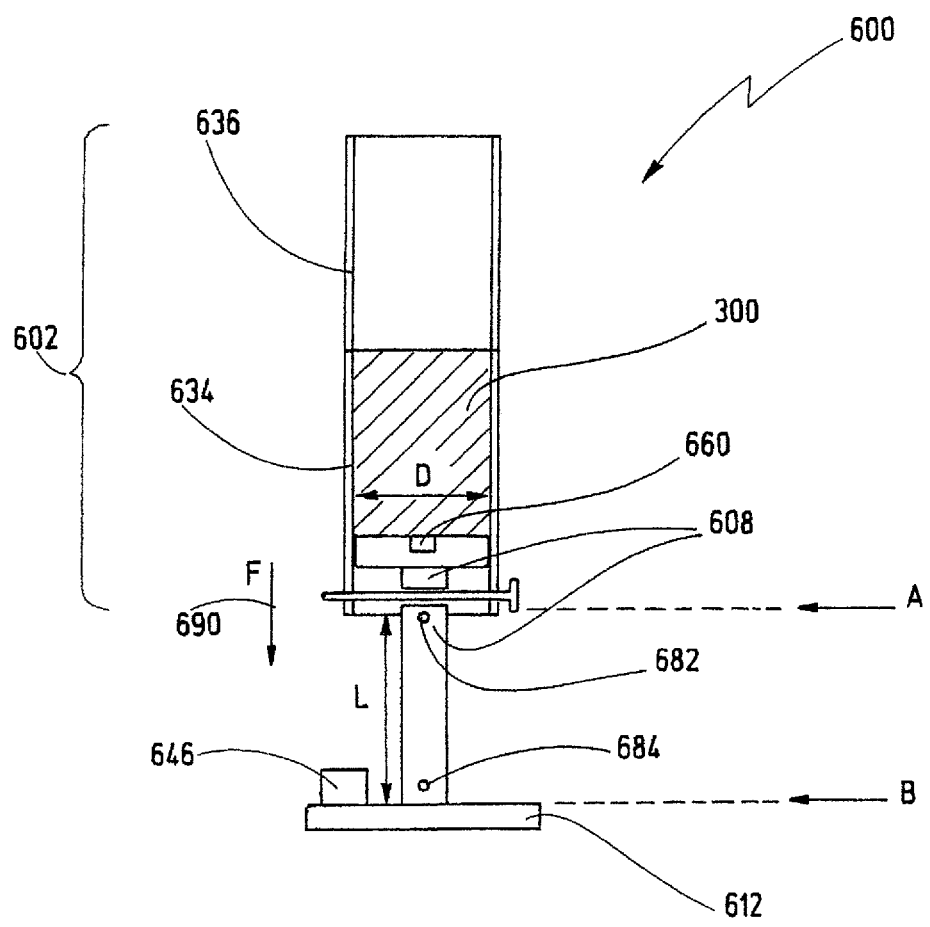
FIG. 6 is a schematic view of a fourth, modified rheometer.

FIG. 6 shows a rheometer 600 wherein as a unit for the determination of a velocity of the relative movement of the high-viscosity material 300 and standard pipe section 602 no laser displacement transducer but a time-measuring apparatus 646 is provided. The basic configuration of the rheometer 600 corresponds to the configuration of the rheometer 100 described with reference to FIGS. 1, 2 was well as FIGS. 3a to 3f. Insofar as the components of the rheometer 600 correspond to those of the rheometer 100, these reference numerals are increased by the number 500. Control switches (682, 684) are assigned to the time-measuring device 646, which switches are switched with a movement of the standard pipe section 602 in correspondence to the arrow 690 from the latch position A into the position B along the piston 608 in order to determine the time duration Δt of the movement of the standard pipe section from position A into the position B.

The rheometer 600 is operated as follows:

With the release of the latching mechanism 637, the standard pipe section filled with the high-viscosity material 300 slides down onto the piston 608. Then, the pressure P, which loads the piston 608, is measured by means of pressure sensor 660 over the time t, and the time duration Δt for this movement is determined with the time measuring device 646. The standard pipe section 608 is accelerated by the weight force to a limit velocity $v_G$.

By realizing the above finding that for conveying the delivery volume Q of some non-thixotropic high-viscosity materials having laminar flow through a pipeline section j, the feeding pressure $P_{FW}$, which is to be developed for overcoming the feeding resistance is sufficient independent of the composition of the high-viscosity material in accordance with the following relationship:

$$P_{FW}(j) = A_j + B_j Q, \quad (9)$$

for the pressure P recorded by the pressure sensor 660 as a function of time t the following will apply:

$$P(t) = \frac{Mg}{\frac{D^2}{4}\pi} - P_{FW}(t) = \frac{4g}{\pi}\frac{M}{D^2} - \left\{A_j + B_j \frac{D^2}{4}\pi v(t)\right\}, \quad (10)$$

wherein v(t) is the instantaneous velocity of the standard pipe section 602 with which the latter glides along the piston 608. In this way, the measured total duration Δt of the movement can be converted into this corresponding limit velocity $v_G$.

By measuring the pressure P(t) resulting for two different limit velocities while using an ancillary load weight the parameters ($A_j$, $B_j$) depending on the high-viscosity material can be concluded from the equation (10).

Figure 7:
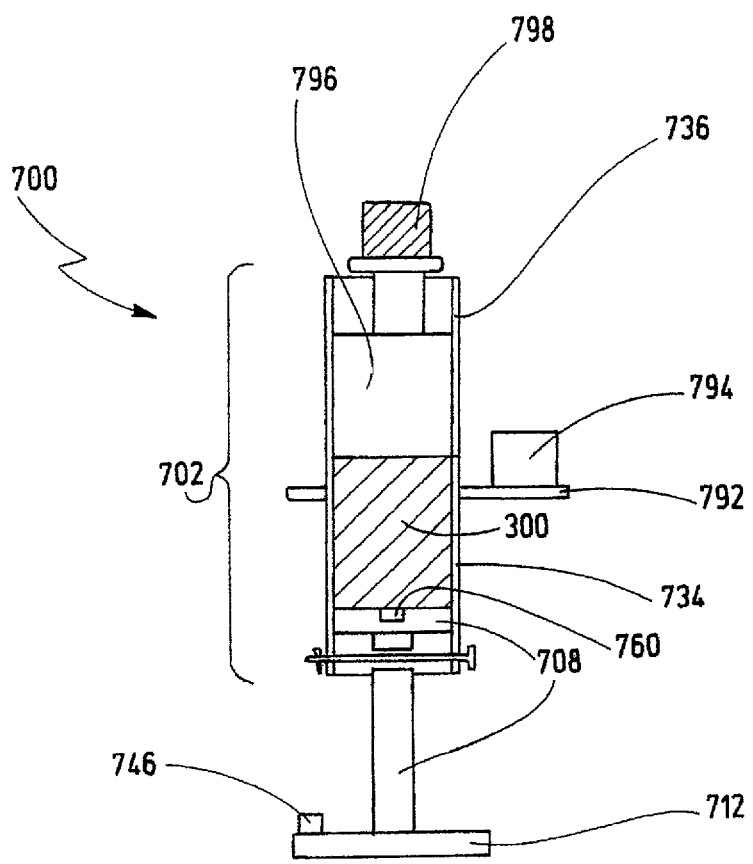
FIG. 7 is a schematic view of a fifth, modified rheometer.

FIG. 7 shows a rheometer 700 which is assembled in correspondence to the rheometer 100 of FIGS. 1 and 2 as well as FIGS. 3a to 3f. With reference to the rheometer 100 of FIG. 1, identical components are identified in rheometer 700 with numerals increased by the number 600. The rheometer 700 has a receiving unit 792 for a load weight 794. It differs from the rheometer 100 of FIG. 1 in that an additional piston 796 having a load weight 798 is provided in the standard pipe section 702 in order to charge the high-viscosity material 300 with an additional pressure in the standard pipe section. This makes it possible to investigate the flow behavior of high-viscosity material which is subjected to pressure.

It is noted that in the rheometers described with respect to FIGS. 1 to 7, also a velocity or time measurement device having a corresponding computer unit can be used as a unit for the determination of a pressure acting on the high-viscosity material via the relative movement of high-viscosity material and the standard pipe section: if the dead weight M of the standard pipe section, which is possibly loaded with a load weight, and the friction force $F_{RK}$, which is conditioned especially by a seal at the piston edge, between the piston and the standard pipe section, are adequately known, then for the case of the stationary movement of the standard pipe section with the limit velocity $v_G$, the pressure P acting on the high-viscosity material via the relative movement of the standard pipe section can be computed as follows:

$$P = \frac{gM - F_{RK}}{\frac{D^2}{4}\pi}, \quad (11)$$

wherein g is the gravitational acceleration and D the diameter of the standard pipe section.

The mass M of the standard pipe section and the load weight can, for example, be determined with scales independently of the rheometric measurement process.

The friction force $F_{RK}$ can be measured with the standard pipe section being empty in that the mass of the standard pipe section required for a free descending movement or the weight force connected therewith is determined. Alternatively to this, it is also possible to determine the friction force via a pressure sensor arranged on the piston, namely in that the measured dynamic pressure is compared to a theoretically expected pressure which would farm on the surface of the piston while neglecting the friction force.

This means that a conclusion can be drawn as to the pressure P, which acts on the high-viscosity material in the standard pipe section, when the standard pipe section descends at the limit velocity $v_G$ with a stationary movement downwards on the piston.

Whether the standard pipe section can be moved with the limit velocity $v_G$ can be determined, for example, via a velocity or time measurement.

Furthermore, it is possible for rheometers described with respect to FIGS. 1 to 7 to provide a pressure-measuring unit with a computer unit for the determination of a velocity of the relative movement of high-viscosity material and standard pipe section.

Figure 8:
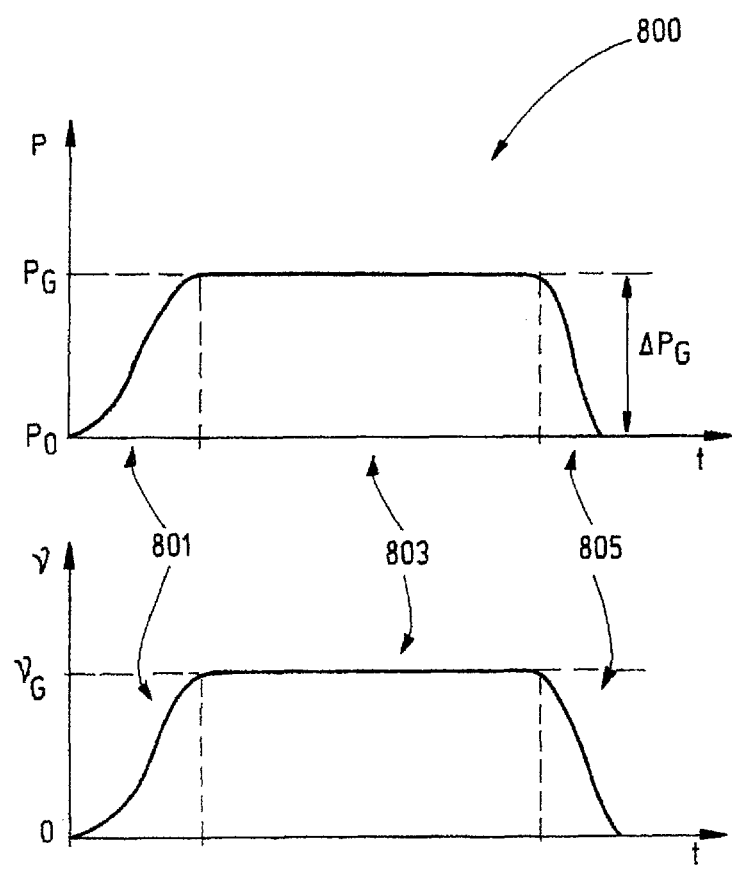
FIG. 8 shows the course of the pressure and velocity in a rheometer.

FIG. 8 shows in a diagram 800 a typical course of the pressure P and the velocity v resulting for the high-viscosity material concrete upon descending of the standard pipe section on the piston.

The pressure P increases first in region 801 up to limit pressure $P_G$ until the standard pipe section has reached the limit velocity $v_G$. In region 803, the pressure P is about constant. P drops abruptly in region 805. The velocity v correspondingly increases to a limit velocity $v_G$ and is constant there until the standard pipe section is abruptly decelerated.

Accordingly, in an idealized manner, the following linear relationship exists between the change of pressure $\Delta P$ and v:

$$v = k\Delta P \quad (12)$$

Wherein:

$$k = \frac{v_G}{\Delta P_G} \quad (13)$$

is an apparatus constant which is dependent only on the configuration of the rheometer. This makes it possible to draw a conclusion as to the velocity v from a pressure P, which is detected at the piston of the rheometer, with which the standard pipe section glides along the piston.

Figure 9:
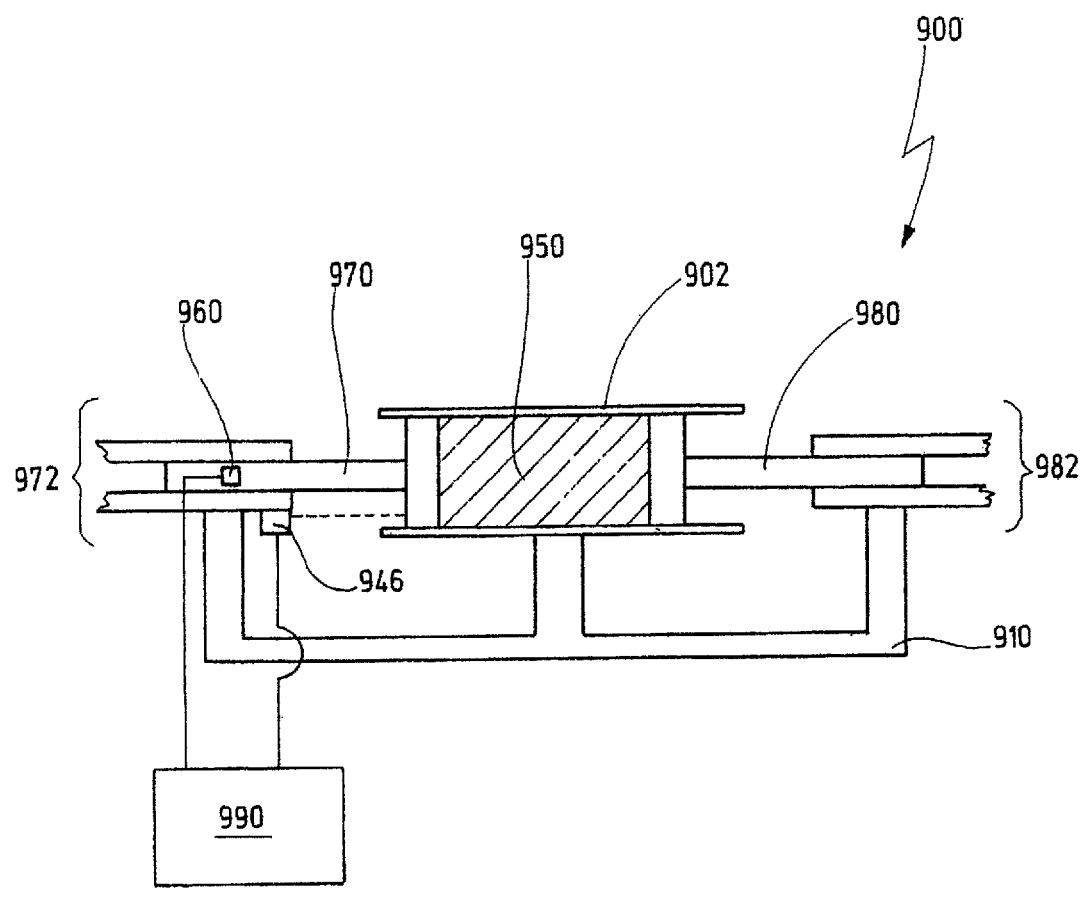
FIG. 9 is a schematic view of a sixth, modified rheometer.

FIG. 9 shows a rheometer 900 having a standard pipe section 902 and a first and a second hydraulically actuated piston (970, 980) having hydraulic drive cylinders (972, 982) which act on a high viscosity volume 950 in a standard pipe section 902 mounted on a carrier unit 910.

By means of the piston 970, it is possible to adjust a drive force F for causing a relative movement of high-viscosity material and standard pipe section 902 which can be measured by a suitable velocity detector 946. A force sensor 960 is provided on the piston 970 for measuring the pressure bearing thereon. The velocity sensor 946 and the force sensor 960 are connected to the computer unit 990 for the purpose of control and signal evaluation.

The piston 980 functions to charge the high-viscosity material in the standard pipe section 902 with an additional load pressure. In this way, by determining the relative velocity of the high-viscosity material, which is accommodated in the standard pipe section, with reference to the piston 970 with a simultaneous measurement of the pressure bearing on the piston 970, in turn the flow behavior of the high-viscosity material at a corresponding adjustable base pressure can be determined.

Figure 10:
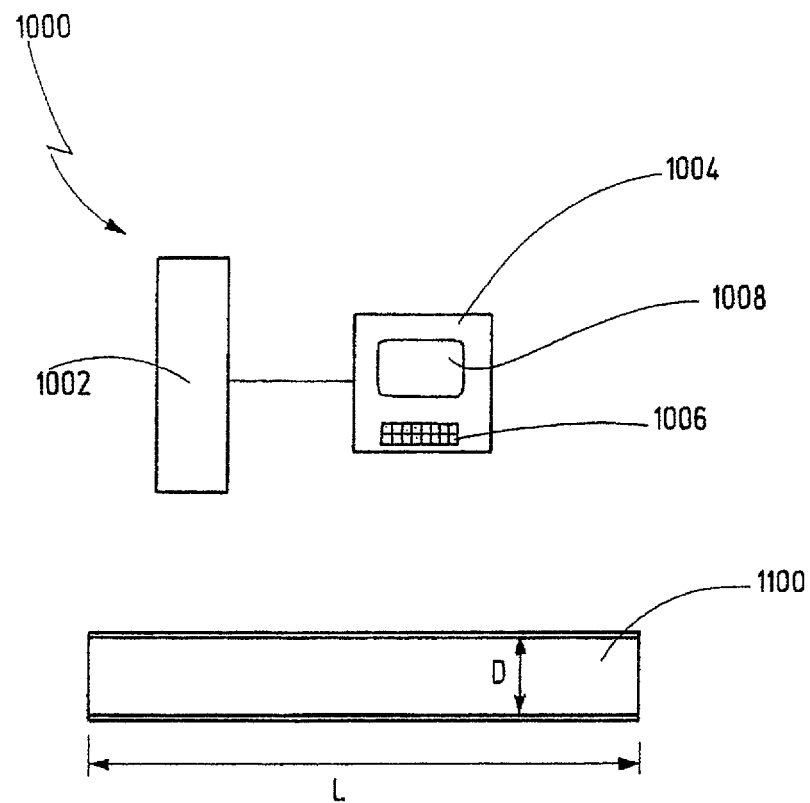
FIG. 10 is an apparatus for estimating the pumping resistance of high-viscosity materials in a pipeline system.

FIG. 10 shows an arrangement 1000 for estimating the feeding pressure $P_{FW}$ at a given delivery volume Q of high-viscosity material, which feeding pressure is needed to overcome the feeding resistance of high-viscosity materials in a pipe opening 1100 having the length L and the diameter D.

The arrangement 1000 includes a rheometer 1002 having a configuration which corresponds to that of the rheometer described with respect to FIGS. 1 to 9. This makes possible a quantified determination of the flow behavior of the high-viscosity material by determining the parameters $\tau_{DS}$ and $b_{DS}$ of equation (3).

The arrangement 1000 includes a computer unit 1004 which is connected to the rheometer 1002. The computer unit 1004 has a data input unit 1006 and a monitor unit 1008. The data input unit 1006 functions for inputting the diameter D and the length L of a pipeline, for which a feeding pressure $P_{FW}$ intended for overcoming the feed resistance is to be estimated, as well as the desired delivery volume Q of high-viscosity material. The computer unit 1004 includes a program to compute the required pressure $P_{FW}$ e.g. on the basis of the equations (3) to (5) in accordance with the following relationship:

$$P_{FW} = \frac{\tau_B}{D}L + \frac{b_B}{D^3}LQ., \quad (17)$$

to then display on the monitor unit 1008 the parameter $\tau_B$ for which a physical significance of the flow limit is applicable, and the parameter $b_B$ which relates to the viscosity of the high-viscosity material.

In summary, it can be concluded: the invention relates to a rheometer 100 for high-viscosity materials as well as to an arrangement and a method for estimating the feeding pressure to be developed for overcoming the feed resistance of the high-viscosity material in a pipeline with such a rheometer 100. The rheometer 100 has a vessel for accommodating the high-viscosity material and a measuring device for the flow behavior of the high-viscosity material in the vessel. The vessel is configured as a standard pipe section 102 fillable with the high-viscosity material 300. In the rheometer 100, a linear relative movement of the standard pipe section 102 and high-viscosity material 300, which is filled into the standard pipe section 102, can be effected at a first velocity and at least with another velocity different from the first velocity. As a measuring device, a unit (146, 147, 148) is provided for the determination of a velocity v of the relative movement of the high-viscosity material 300 and the standard pipe section 102, and a unit 160 is provided for the determination of a pressure P acting via the relative movement of the high-viscosity material 300 and the high-viscosity material 300 acting on the standard pipe section 102.

It is understood that the foregoing description is that of the preferred embodiments of the invention and that various changes and modifications may be made thereto without departing from the spirit and scope of the invention as defined in the appended claims.

What is claimed is:

1. A rheometer for high-viscosity materials, the rheometer comprising:
a vessel assembly including a piston and a pipe section fillable with the high-viscosity material and said pipe section being movable at a velocity (v) relative to said piston and said high-viscosity material;
said piston being a stationary piston arranged in said pipe section so as to cause the high-viscosity material to act on said piston with a pressure (P);
a measuring arrangement including a first unit for measuring said pressure (P) and a second measuring unit for measuring said velocity (v) as said pipe section moves relative to said piston and said high-viscosity material; and,
a computer unit for carrying out a computation of the flow behavior of said high-viscosity material in said vessel assembly based on said velocity (v) and said pressure (P).

2. The rheometer of claim 1, further comprising a constraining guide for linearly guiding the movement of said pipe section from a first position (A) to a second position (B).

3. The rheometer of claim 2, further comprising a latching mechanism for fixing said pipe section in said first position (A) and/or said second position (B).

4. The rheometer of claim 3, further comprising a carrier unit for accommodating said pipe section and said piston thereon with said piston being fixedly connected to said carrier unit; and, said carrier unit including an adjusting device for vertically aligning said pipe section.

5. The rheometer of claim 1, wherein said pressure (P) acts on said piston because of the relative movement of the high-viscosity material and said pipe section; and, said first unit for measuring said pressure (P) includes one of a pressure sensor mounted on said piston and a force sensor mounted on said piston.

6. The rheometer of claim 1, further comprising drive means for generating a drive force (F) acting on said pipe section to effect said relative movement.

7. The rheometer of claim 6, said drive means being configured for generating said drive force (F) to have different magnitudes.

8. The rheometer of claim 6, wherein said drive means comprises a load weight for generating said drive force (F).

9. The rheometer of claim 8, wherein said load weight is an adjustable load weight.

10. The rheometer of claim 1, wherein said piston is a first piston; and, said rheometer further comprises a second piston for acting on said high-viscosity material in said pipe section for generating the relative movement of said pipe section and high-viscosity material; and, said second piston being mounted so as to be movable relative to said pipe section.

11. The rheometer of claim 10, further comprising means for generating a drive force (F) acting on said second piston to generate a relative movement of said pipe section and said second piston.

12. The rheometer of claim 1, wherein said pipe section is configured to have a reduction in the inner diameter thereof.

13. The rheometer of claim 1, wherein said pipe section is configured to have a bend formed therein.

14. The rheometer of claim 1, wherein said pipe section is made, at least in part, of transparent material.

15. The rheometer of claim 14, wherein said transparent material is transparent plastic.

16. The rheometer of claim 1, wherein said pipe section is made of two pipe section segments; and, said pipe section includes means for facilitating the joining and separation of said two pipe section segments.

17. The rheometer of claim 1, further comprising means for charging said high-viscosity material accommodated in said pipe section with a static pressure.

18. The rheometer of claim 1, wherein said high-viscosity material is concrete.

19. A method for estimating the feeding pressure ($P_{FW}$) which is to be developed for overcoming the feeding resistance of high-viscosity material in a pipeline, the method comprising the steps of:

(a) filling a pipe section with the high-viscosity material to be fed;

(b) moving said pipe section relative to the high-viscosity material filled in said pipe section at a velocity (v) while a pressure (P) acts on said high-viscosity material;

(c) determining said velocity (v) and said pressure (P) acting on said high-viscosity material during the movement of said pipe section;

(d) repeating steps (b) and (c) to obtain respective sets of values of said velocity (v) and said pressure (P);

and, computing the feeding resistance of the high-viscosity material based on the determined velocities (v) of the relative movement of the high-viscosity material and the pipe section and from the determined pressure values (P).

20. The method of claim 19, wherein the value of said pressure (P), which acts on the high-viscosity material, is determined via a velocity measurement or a time measurement.

21. The method of claim 20, wherein said velocity (v) of the relative movement of the high-viscosity material and pipe section is determined via a pressure measurement.

22. The method of claim 19, wherein said high-viscosity material is concrete.

23. An arrangement for determining the feeding resistance of high-viscosity material in a pipeline system with a rheometer comprising:

a vessel assembly including a pipe section fillable with the high-viscosity material and a piston movable at a velocity (v) relative to said pipe section and said high-viscosity material;

said piston being a stationary piston arranged in said pipe section so as to cause the high-viscosity material to act on said piston with a pressure (P);

a measuring arrangement including a first unit for measuring said pressure (P) and a second unit for measuring said velocity (v) as said pipe section moves relative to said piston and said high-viscosity material; and, a computer unit for carrying out a computation of the flow behavior of said high-viscosity material in said vessel assembly based on said velocity (v) and said pressure (P).

24. The arrangement of claim 23, wherein said high-viscosity material is concrete and said pipe section has a diameter corresponding to the diameter of the pipes of said pipeline system.

* * * * *